US011916256B2

(12) United States Patent
Viavattine et al.

(10) Patent No.: US 11,916,256 B2
(45) Date of Patent: Feb. 27, 2024

(54) BATTERY ASSEMBLY

(71) Applicant: Medtronic, Inc., Minneapolis, MN (US)

(72) Inventors: Joseph J. Viavattine, Vadnais Heights, MN (US); Erik J. Hovland, Minnetonka, MN (US)

(73) Assignee: Medtronic, Inc., Minneapolis, MN (US)

( * ) Notice: Subject to any disclaimer, the term of this patent is extended or adjusted under 35 U.S.C. 154(b) by 156 days.

(21) Appl. No.: 17/172,903

(22) Filed: Feb. 10, 2021

(65) Prior Publication Data

US 2022/0255198 A1    Aug. 11, 2022

(51) Int. Cl.
| | |
|---|---|
| *H01M 50/538* | (2021.01) |
| *H01M 50/533* | (2021.01) |
| *H01M 50/184* | (2021.01) |
| *H01M 50/174* | (2021.01) |
| *H01M 50/536* | (2021.01) |

(52) U.S. Cl.
CPC ....... *H01M 50/538* (2021.01); *H01M 50/174* (2021.01); *H01M 50/184* (2021.01); *H01M 50/533* (2021.01); *H01M 50/536* (2021.01)

(58) Field of Classification Search
CPC .......... H01M 50/172–184; H01M 50/533–538
See application file for complete search history.

(56) References Cited

U.S. PATENT DOCUMENTS

| | | | |
|---|---|---|---|
| 5,618,318 | A | 4/1997 | Reddy et al. |
| 6,461,762 | B1 | 10/2002 | Yang et al. |
| 6,692,866 | B2 | 2/2004 | Watanabe et al. |
| 7,035,078 | B1 | 4/2006 | Viavattine |
| 8,142,928 | B2 | 3/2012 | Blomgren et al. |

(Continued)

FOREIGN PATENT DOCUMENTS

| | | |
|---|---|---|
| GB | 2574804 A | 12/2019 |
| WO | 2016205663 A1 | 12/2016 |
| WO | 2019010323 A1 | 1/2019 |

OTHER PUBLICATIONS

Linder, "Maybe the Galaxy Fold Should Have Used This Foldable Battery," Popular Mechanics, Sep. 27, 2019, 8 pp.

(Continued)

*Primary Examiner* — Matthew T Martin
*Assistant Examiner* — Unique Jenevieve Luna
(74) *Attorney, Agent, or Firm* — Shumaker & Sieffert, P.A.

(57) ABSTRACT

In some examples, an assembly for a medical device. The assembly includes a first electrode comprising a first conductive tab, and a first current collector; a second electrode including a second conductive tab, a second current collector, a third current collector, and at least one connector connecting the second current collector to the third current collector, wherein the second current collector and the third current collector are folded over each other about the at least one connector, wherein the second conductive tab is coupled to the second current collector, and wherein the third current collector is electrically coupled to second conductive tab via the at least one connector and the second current collector; and a foil package being sealed over the first conductive tab and the second conductive tab to partially enclose the first electrode and second electrode.

21 Claims, 10 Drawing Sheets

(56) References Cited

U.S. PATENT DOCUMENTS

| | | |
|---|---|---|
| 8,940,430 B2 | 1/2015 | Phillips et al. |
| 9,236,590 B2 | 1/2016 | Aoki |
| 2006/0092593 A1 | 5/2006 | Viavattine |
| 2013/0029205 A1 | 1/2013 | Adams et al. |
| 2013/0131744 A1 | 5/2013 | Viavattine |
| 2013/0131745 A1 | 5/2013 | Viavattine |
| 2014/0030590 A1 | 1/2014 | Wang et al. |
| 2016/0158556 A1* | 6/2016 | Viavattine ............... H01M 6/46 607/9 |
| 2017/0058389 A1 | 3/2017 | Gayden et al. |
| 2017/0214057 A1* | 7/2017 | Kotik ................ H01M 10/0525 |
| 2018/0269437 A1 | 9/2018 | Zhang et al. |
| 2019/0273237 A1 | 9/2019 | Kawai et al. |
| 2020/0014025 A1 | 1/2020 | Zagars et al. |
| 2020/0044274 A1 | 2/2020 | He et al. |
| 2020/0066462 A1 | 2/2020 | Kapelushnik |

OTHER PUBLICATIONS

Song et al., "Origami Lithium-Ion Batteries," Nature Communications, vol. 5, No. 3140, Jan. 28, 2014, 25 pp.

Suresh, "Foldable, High Energy Density Lithium Ion Batteries," A Thesis Submitted to the Graduate Faculty of Rensselaer Polytechnic Institute, Jul. 2017, 24 pp.

International Search Report and Written Opinion of International Application No. PCT/US2022/011547, dated Apr. 21, 2022, 12 pp.

* cited by examiner

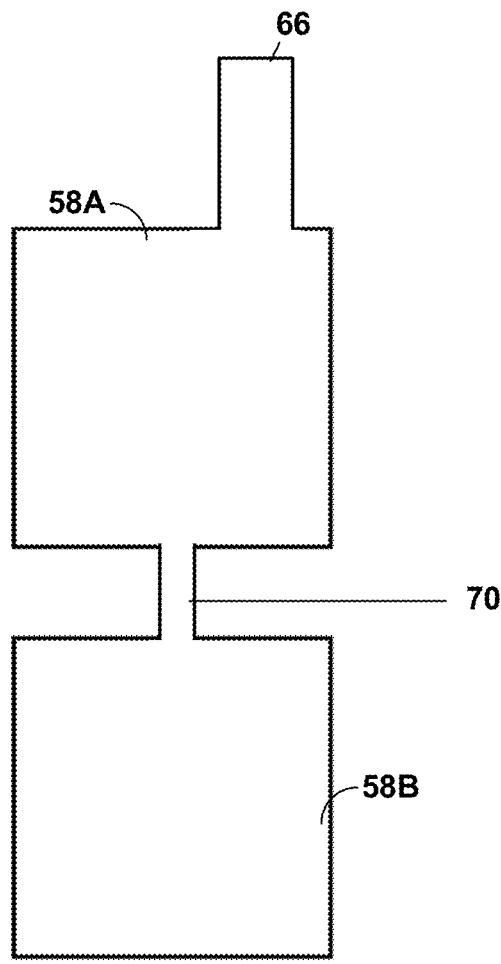
FIG. 5
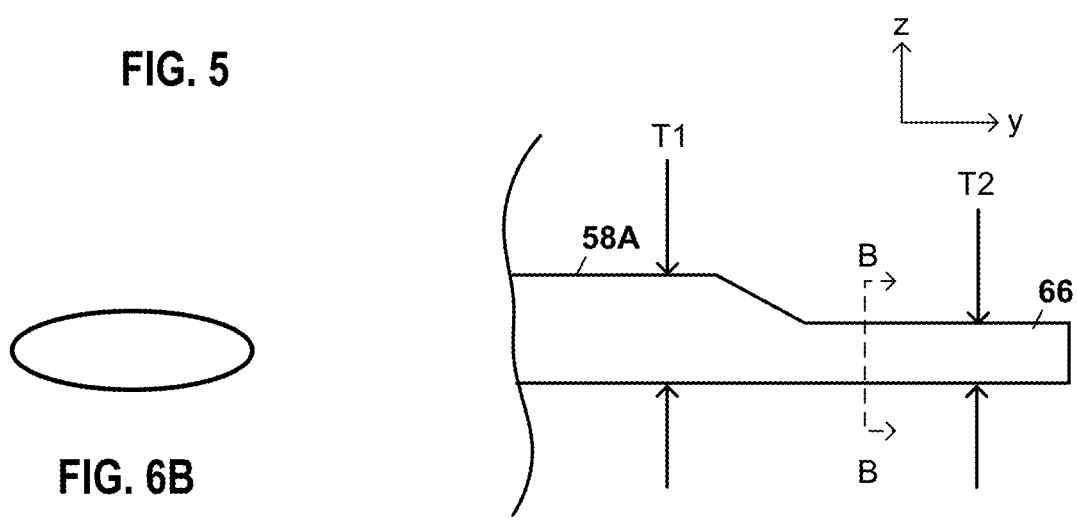
FIG. 6B
FIG. 6A

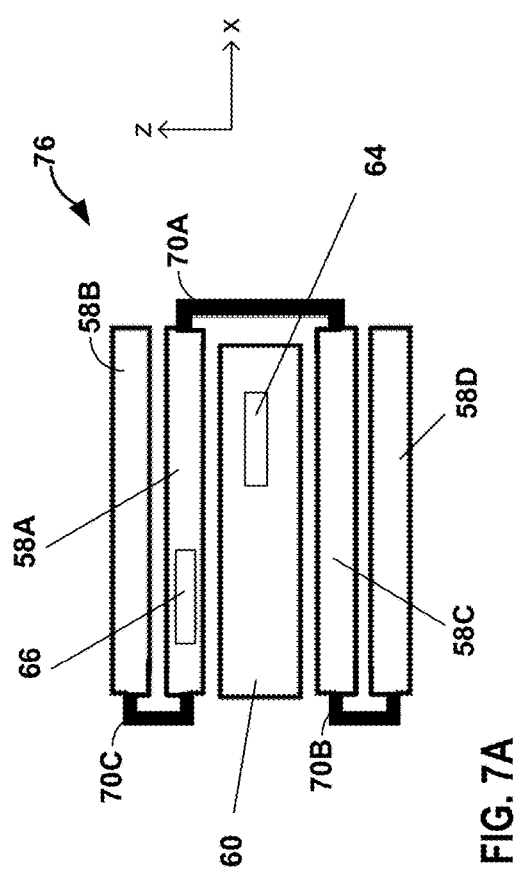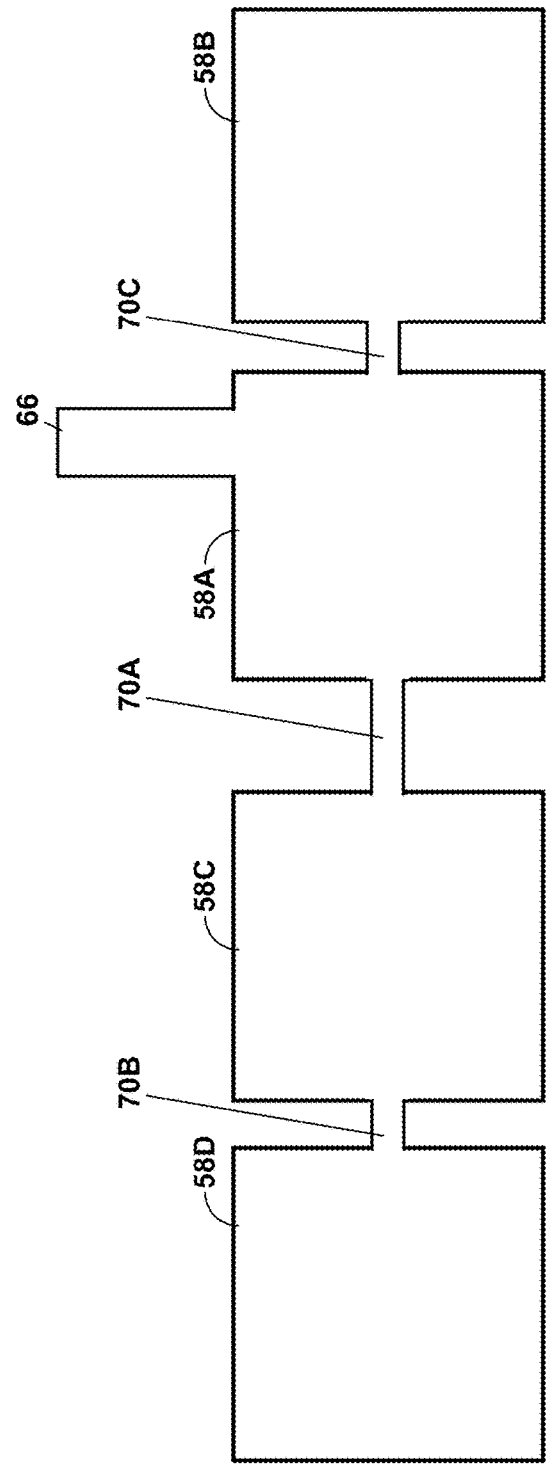
FIG. 7A
FIG. 7B

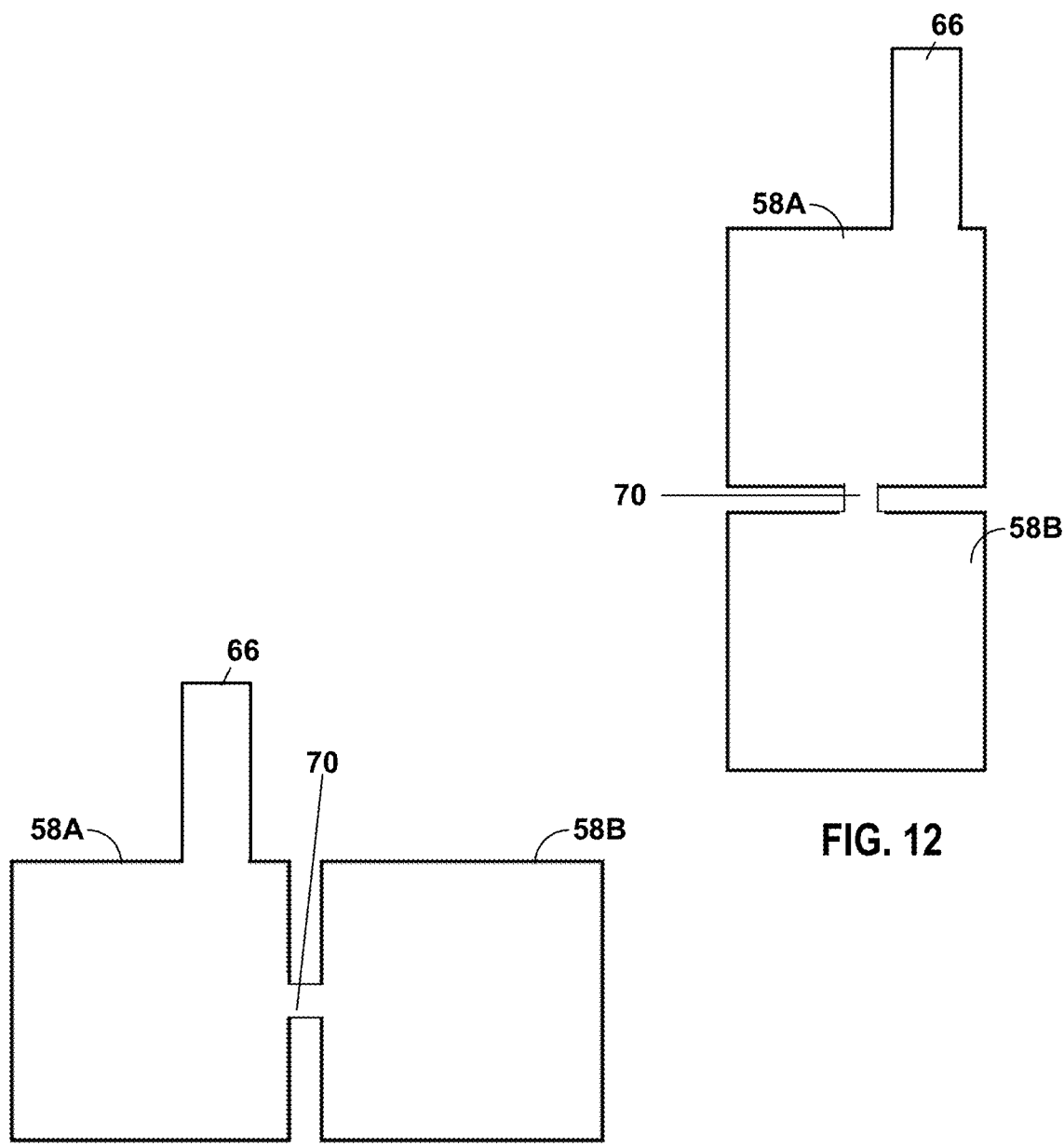
FIG. 12
FIG. 11
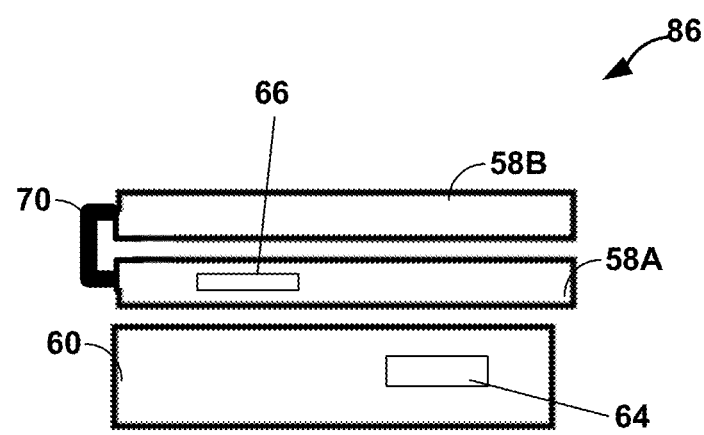
FIG. 10

BATTERY ASSEMBLY

TECHNICAL FIELD

The disclosure relates to batteries, such as, batteries for use in medical devices.

BACKGROUND

Medical devices such as implantable medical devices (IMDs) include a variety of devices that deliver therapy (such as electrical simulation or drugs) to a patient, monitor a physiological parameter of a patient, or both. IMDs typically include a number of functional components encased in a housing. The housing is implanted in a body of the patient. For example, the housing may be implanted in a pocket created in a torso of a patient. The housing may include various internal components such as one or more energy storage devices to supply energy for electrical stimulation delivered to a patient and/or to power circuitry for monitoring a physiological parameter of a patient and controlling the functionality of the medical device.

Example energy storage devices that supply operational power may include batteries and capacitors. In the examples, the energy storage devices may include electrochemical cells that function to provide and/or store energy. In some examples, the energy storage devices may be enclosed by foil packs that are configured to isolate or otherwise separate components of the electrochemical cell from an environment surrounding an exterior of the foil pack. A heat-sealing process may be employed to seal portions of the foil pack once the energy storage device has been located within the foil pack.

SUMMARY

In one example, the disclosure is directed to an assembly comprising a first electrode comprising a first conductive tab, a first current collector, and a first active material on the first current collector; a second electrode comprising a second conductive tab, a second current collector, a third current collector, a second active material on the second current collector and the third current collector, and at least one connector connecting the second current collector to the third current collect, wherein the second current collector and the third current collector are folded over each other about the at least one connector, wherein the second conductive tab is coupled to the second current collector, and wherein the third current collector is electrically coupled to second conductive tab via the at least one connector and the second current collector; and a foil package being sealed over the first conductive tab and the second conductive tab to partially enclose the first electrode and second electrode.

In another example, the disclosure is directed to a method positioning a first electrode relative to a second electrode, wherein the first electrode comprises a first conductive tab, a first current collector, and a first active material on the first current collector, and wherein the second electrode comprises a second conductive tab, a second current collector, a third current collector, a second active material on the second current collector and the third current collector, and at least one connector connecting the second current collector to the third current collect, wherein the second current collector and the third current collector are folded over each other about the at least one connector, wherein the second conductive tab is coupled to the second current collector, and wherein the third current collector is electrically coupled to second conductive tab via the at least one connector and the second current collector; and heat sealing a foil package over the first conductive tab and the second conductive tab to partially enclose the first electrode and second electrode.

The details of one or more examples of the disclosure are set forth in the accompanying drawings and the description below. Other features, objects, and advantages of the disclosure will be apparent from the description and drawings, and from the claims.

BRIEF DESCRIPTION OF DRAWINGS

FIG. 5 is a conceptual schematic diagram illustrating an example electrode in accordance with examples of the disclosure.

FIGS. 6A and 6B are conceptual schematic diagrams illustrating a portion of an example electrode in accordance with examples of the disclosure.

FIGS. 7A and 7B are conceptual schematic diagrams illustrating example electrodes in accordance with examples of the disclosure.

FIGS. 10-14 are conceptual schematic diagrams illustrating other example electrodes in accordance with examples of the disclosure.

DETAILED DESCRIPTION

Figure 1:
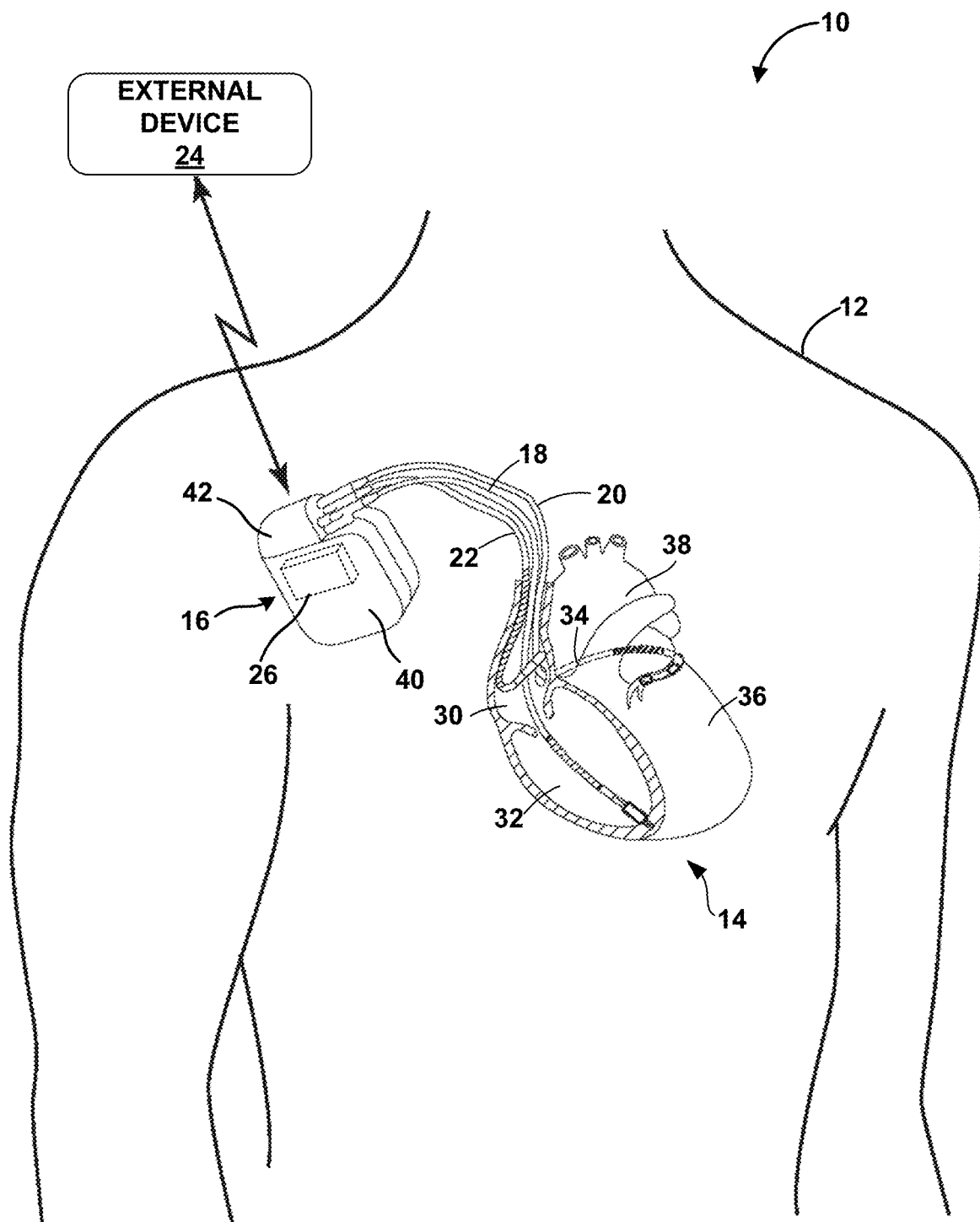
FIG. 1 is a conceptual diagram that illustrates an example medical device system that may be used to deliver therapy to a patient.

In some examples, the disclosure describes example assemblies including a foil pack and an energy storage device enclosed by the foil pack, and techniques for making such assemblies. For ease of description, example energy storage devices are primarily described in the context of batteries in the form of electrochemical cells. However, other examples in which the energy storage devices function as capacitors are contemplated.

A variety of medical devices may utilize one or more energy storage devices as a power source for operational power. For example, an implantable medical device (IMD) that provides cardiac rhythm management therapy to a patient may include a battery to supply power for the generation of electrical therapy or other functions of the IMD. For ease of illustration, examples of the present disclosure will be described primarily with regard to energy storage device assemblies including batteries that are employed in IMDs that provide cardiac rhythm management therapy. However, as will be apparent from the description herein, examples of the disclosure are not limited to IMDs that provide such therapy. For example, in some instances, one or more of the example energy storage assemblies described herein may be used by a medical device configured to deliver electrical stimulation to a patient in the form of neurostimulation therapy (e.g., spinal cord stimulation therapy, deep brain stimulation therapy, peripheral nerve stimulation therapy, peripheral nerve field stimulation therapy, pelvic floor stimulation therapy, and the like). In some examples, example energy storage assemblies of this disclosure may be employed in medical devices configured to monitor one or more patient physiological parameters, e.g., by monitoring electrical signals of the patient, alone or in conjunction with the delivery of therapy to the patient. Furthermore, example energy storage assemblies of the disclosure are not limited to medical devices and may be employed in any device in which such an energy storage assembly may be used to supply operational power to the device from a sealed foil pack enclosure.

In some examples, battery assemblies for IMDs connect current collectors of the battery electrodes from within a rigid battery enclosure to other components of the IMD directly to a feedthrough or jumper in order to get the energy out of the battery enclosure. Such interconnects may be separate components connected to the current collectors by welds (e.g., by laser, resistance, or ultrasonic welding). The welding process for the interconnects may result in undesirable heat generation, which may potentially damage neighboring components of the IMD. Additionally, or alternatively, the welds may be susceptible to failure if too weak. Furthermore, the welding process may result in additional manufacturing costs e.g., resulting from the additional parts, equipment, and time to make such battery assemblies and IMDs incorporating such assemblies.

In some examples, a foil package (also referred to as a foil pack) enclosing the components the battery assembly (e.g., electrodes and electrolyte) may be employed to fluidly isolate the battery assembly components from an environment surrounding an exterior of the foil pack. For example, the battery assembly may be configured for placement within the housing of a larger device such as an implantable medical device or other device, with the foil pack substantially isolating the battery assembly from other components within the housing of the larger device. The foil pack may provide an enclosure with a hermetic and/or liquid tight boundary depending on the device requirements and design.

In accordance with some examples of the disclosure, an assembly may include a foil pack that encloses the electrodes and electrolyte of a battery assembly that forms an electrochemical cell. Such energy storage devices that use a foil pack may employ a flat metal strip or tab to serve as the feedthrough to get energy out of the battery within the foil pack enclosure. These electrically conductive tabs may be sealed between the two outer layers of laminated foil which serve as the foil pack enclosure. The current collectors used for anodes and/or cathode of the energy storage devices assemblies may be formed of relatively thin conductive sheets, such as, thin etched metal sheets. Given the relatively flat nature of the conductive tabs extending from the current collectors, the conductive tabs may be integrated with the current collectors. For example, the current collector for the anode and/or cathode of the battery assembly may be formed of a thin metal sheet that also defines the thin metal conductive tab that extends out of the foil pack enclosure. In some examples, such as design may eliminate the need for interconnect welding, extra parts, and the challenges that come along with creating more electrical connections.

Additionally, or alternatively, examples of the disclosure include battery assemblies that include electrode(s) having multiple current collector plates that are folded on each other via connectors that connect the respective plates. For example, a battery assembly may include a cathode including multiple cathode plates connected to each other via connectors that connect the respective cathode plates. In some examples, the multiple cathode current collector plates may be formed from the same thin metal sheet with one or more connectors connecting the cathode current collector plates both electrically and physically. With the connectors connecting the respective cathode current collector plates, each of the cathode current collector plates may be electrically connected to the same single conductive tab for the cathode, e.g., that is integrally formed with only one of the cathode current collector plates. During the manufacturing process, the multiple cathode plates connected by one or more connectors may be formed, e.g., by etching a thin, planar metal sheet to the desired shape, coating the respective cathode plates with an active material, and then folding the cathode plates about the connectors to form a cathode with multiple plates in a folded configuration. In some examples, such a design may allow for the cathode plate thickness (e.g., cathode current collector plus active material thickness) to be less dependent on total energy by changing the total area of the electrode.

As an illustrative example, a battery assembly may include an anode with a single anode plate including an anode current collector and active material stacked on a cathode with a single cathode plate including a cathode current collector and active material (e.g., with each plate being similar to that shown in FIG. 9) enclosed within a foil pack, where the battery assembly forms a cell with some capacity. In such an example, the thickness of the cathode plate may expand more in-plane upon discharge and may stress the foil pack seal. Making a cathode with two thinner cathode plates (either with a connection between the two plates or two separate plates) may reduce the in-plane expansion of the cathode. Furthermore, if a "butterfly" cathode is positioned on either side of the anode (like a cathode plate/anode plate/cathode plate configuration shown FIGS. 3B and 3C) the power of the battery may be approximately doubled. Further extending the concept to four cathode plates, as in the example shown in FIGS. 7A and 7B, may thin out/reduce the thickness of the cathode plates even more, e.g., with the cathode current collector thickness likely being the same for each of these options. In this last example, the "outer wings" or the two cathode plates furthest from the center are folded upon the inner cathode plates. While these cathode plates are not directly adjacent to the anode plate, the plates still discharge and provide some additional power.

FIG. 1 is a conceptual diagram that illustrates an example medical device system 10 that may be used to provide electrical therapy to a patient 12. Patient 12 ordinarily, but not necessarily, will be a human. System 10 may include an IMD 16, and an external device 24. In the example illustrated in FIG. 1, IMD 16 has energy storage device assembly 26 positioned within an outer housing 40 of the IMD 16. Energy storage device assembly 26 may function as a battery (e.g., primary or secondary) or capacitor assembly including one or more electrochemical cells that supply operational power for IMD 16. As described further below, energy storage device assembly 26 includes foil pack 50 that encloses components of an electrochemical cell such as electrodes (anode and cathode) and an electrolyte.

While the examples in the disclosure are primarily described with regard to energy storage device assembly 26 positioned within housing 40 of IMD 16 for delivery of electrical therapy to heart of patient 12, in other examples, energy storage device assembly 26 may be utilized with other implantable medical devices. For example, energy storage device assembly 26 may be utilized with an implantable drug delivery device, an implantable monitoring device that monitors one or more physiological parameter of patient 12, an implantable neurostimulator (e.g., a spinal cord stimulator, a deep brain stimulator, a pelvic floor stimulator, a peripheral nerve stimulator, or the like), or the like. Moreover, while examples of the disclosure are primarily described with regard to implantable medical devices, examples are not limited as such. Rather, some examples of the energy storage device assemblies described herein may be employed in any medical device including non-implantable medical devices. For example, an example energy storage device assembly may be employed to supply power to a medical device configured delivery therapy to a patient externally or via a transcutaneously implanted lead or drug delivery catheter the requires a high reliability power source.

In the example depicted in FIG. 1, IMD 16 is connected (or "coupled") to leads 18, 20, and 22. IMD 16 may be, for example, a device that provides cardiac rhythm management therapy to heart 14, and may include, for example, an implantable pacemaker, cardioverter, and/or defibrillator that provides therapy to heart 14 of patient 12 via electrodes coupled to one or more of leads 18, 20, and 22. In some examples, IMD 16 may deliver pacing pulses, but not cardioversion or defibrillation shocks, while in other examples, IMD 16 may deliver cardioversion or defibrillation shocks, but not pacing pulses. In addition, in further examples, IMD 16 may deliver pacing pulses, cardioversion shocks, and defibrillation shocks.

IMD 16 may include electronics and other internal components necessary or desirable for executing the functions associated with the device. In one example, IMD 16 includes one or more of processing circuitry, memory, a signal generation circuitry, sensing circuitry, telemetry circuitry, and a power source. In general, memory of IMD 16 may include computer-readable instructions that, when executed by a processor of the IMD, cause it to perform various functions attributed to the device herein. For example, processing circuitry of IMD 16 may control the signal generator and sensing circuitry according to instructions and/or data stored on memory to deliver therapy to patient 12 and perform other functions related to treating condition(s) of the patient with IMD 16.

IMD 16 may include or may be one or more processors or processing circuitry, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" and "processing circuitry" as used herein may refer to any of the foregoing structure or any other structure suitable for implementation of the techniques described herein.

Memory may include any volatile or non-volatile media, such as a random-access memory (RAM), read only memory (ROM), non-volatile RAM (NVRAM), electrically erasable programmable ROM (EEPROM), flash memory, and the like. Memory may be a storage device or other non-transitory medium.

The signal generation circuitry of IMD 16 may generate electrical therapy signals that are delivered to patient 12 via electrode(s) on one or more of leads 18, 20, and 22, in order to provide pacing signals or cardioversion/defibrillation shocks, as examples. The sensing circuitry of IMD 16 may monitor electrical signals from electrode(s) on leads 18, 20, and 22 of IMD 16 in order to monitor electrical activity of heart 14. In one example, the sensing circuitry may include switching circuitry to select which of the available electrodes on leads 18, 20, and 22 of IMD 16 are used to sense the heart activity. Additionally, the sensing circuitry of IMD 16 may include multiple detection channels, each of which includes an amplifier, as well as an analog-to-digital converter for digitizing the signal received from a sensing channel (e.g., electrogram signal processing by processing circuitry of the IMD).

Telemetry circuitry of IMD 16 may be used to communicate with another device, such as external device 24. Under the control of the processing circuitry of IMD 16, the telemetry circuitry may receive downlink telemetry from and send uplink telemetry to external device 24 with the aid of an antenna, which may be internal and/or external.

The various components of IMD 16 may be coupled to a power source such as energy storage device assembly 26, which may include a lithium primary battery. Energy storage device assembly 26 may be capable of holding a charge for several years. In general, energy storage device assembly 26 may supply power to one or more electrical components of IMD 16, such as, e.g., the signal generation circuitry, to allow IMD 16 to deliver therapy to patient 12, e.g., in the form of monitoring one or more patient parameters, delivery of electrical stimulation, or delivery of a therapeutic drug fluid. Energy storage device assembly 26 may include foil pack 50 that encloses one or more lithium-containing anodes and cathodes including an active material that electrochemically reacts with the lithium within an electrolyte to generate power.

Leads 18, 20, 22 that are coupled to IMD 16 may extend into the heart 14 of patient 12 to sense electrical activity of heart 14 and/or deliver electrical therapy to heart 14. In the example shown in FIG. 1, right ventricular (RV) lead 18 extends through one or more veins (not shown), the superior vena cava (not shown), and right atrium 30, and into right ventricle 32. Left ventricular (LV) coronary sinus lead 20 extends through one or more veins, the vena cava, right atrium 30, and into the coronary sinus 34 to a region adjacent to the free wall of left ventricle 36 of heart 14. Right atrial (RA) lead 22 extends through one or more veins and the vena cava, and into the right atrium 30 of heart 14. In other examples, IMD 16 may deliver therapy to heart 14 from an extravascular tissue site in addition to or instead of delivering therapy via electrodes of intravascular leads 18, 20, 22. In the illustrated example, there are no electrodes located in left atrium 36. However, other examples may include electrodes in left atrium 36.

IMD 16 may sense electrical signals attendant to the depolarization and repolarization of heart 14 (e.g., cardiac signals) via electrodes (not shown in FIG. 1) coupled to at least one of the leads 18, 20, and 22. In some examples, IMD 16 provides pacing pulses to heart 14 based on the cardiac signals sensed within heart 14. The configurations of electrodes used by IMD 16 for sensing and pacing may be unipolar or bipolar. IMD 16 may also deliver defibrillation therapy and/or cardioversion therapy via electrodes located on at least one of the leads 18, 20, and 22. IMD 16 may detect arrhythmia of heart 14, such as fibrillation of ventricles 32 and 36, and deliver defibrillation therapy to heart 14 in the form of electrical shocks. In some examples, IMD 16 may be programmed to deliver a progression of therapies (e.g., shocks with increasing energy levels) until a fibrillation of heart 14 is stopped. IMD 16 may detect fibrillation by employing one or more fibrillation detection techniques known in the art. For example, IMD 16 may identify cardiac parameters of the cardiac signal (e.g., R-waves), and detect fibrillation based on the identified cardiac parameters.

In some examples, external device 24 may be a handheld computing device or a computer workstation. External device 24 may include a user interface that receives input from a user. The user interface may include, for example, a keypad and a display, which may be, for example, a cathode ray tube (CRT) display, a liquid crystal display (LCD) or light emitting diode (LED) display. The keypad may take the form of an alphanumeric keypad or a reduced set of keys associated with particular functions. External device 24 can additionally or alternatively include a peripheral pointing device, such as a mouse, via which a user may interact with the user interface. In some embodiments, a display of external device 24 may include a touch screen display, and a user may interact with external device 24 via the display.

A user, such as a physician, technician, other clinician or caregiver, or the patient, may interact with external device 24 to communicate with IMD 16. For example, the user may interact with external device 24 to retrieve physiological or diagnostic information from IMD 16. A user may also interact with external device 24 to program IMD 16 (e.g., select values for operational parameters of IMD 16).

External device 24 may communicate with IMD 16 via wireless communication using any techniques known in the art. Examples of communication techniques may include, for example, low frequency or radiofrequency (RF) telemetry, but other techniques are also contemplated. In some examples, external device 24 may include a communication head that may be placed proximate to the patient's body near the IMD 16 implant site in order to improve the quality or security of communication between IMD 16 and external device 24.

In the example depicted in FIG. 1, IMD 16 is connected (or "coupled") to leads 18, 20, and 22. In the example, leads 18, 20, and 22 are connected to IMD 16 using the connector block 42. For example, leads 18, 20, and 22 are connected to IMD 16 using the lead connector ports in connector block 42. Once connected, leads 18, 20, and 22 are in electrical contact with the internal circuitry of IMD 16. Energy storage device assembly 26 may be positioned within the outer housing 40 of IMD 16. Housing 40 may be hermetically sealed and biologically inert. In some examples, outer housing 40 may be formed from a conductive material. For example, housing 40 may be formed from a material including, but not limited to, titanium, stainless steel, among others.

Figure 2:
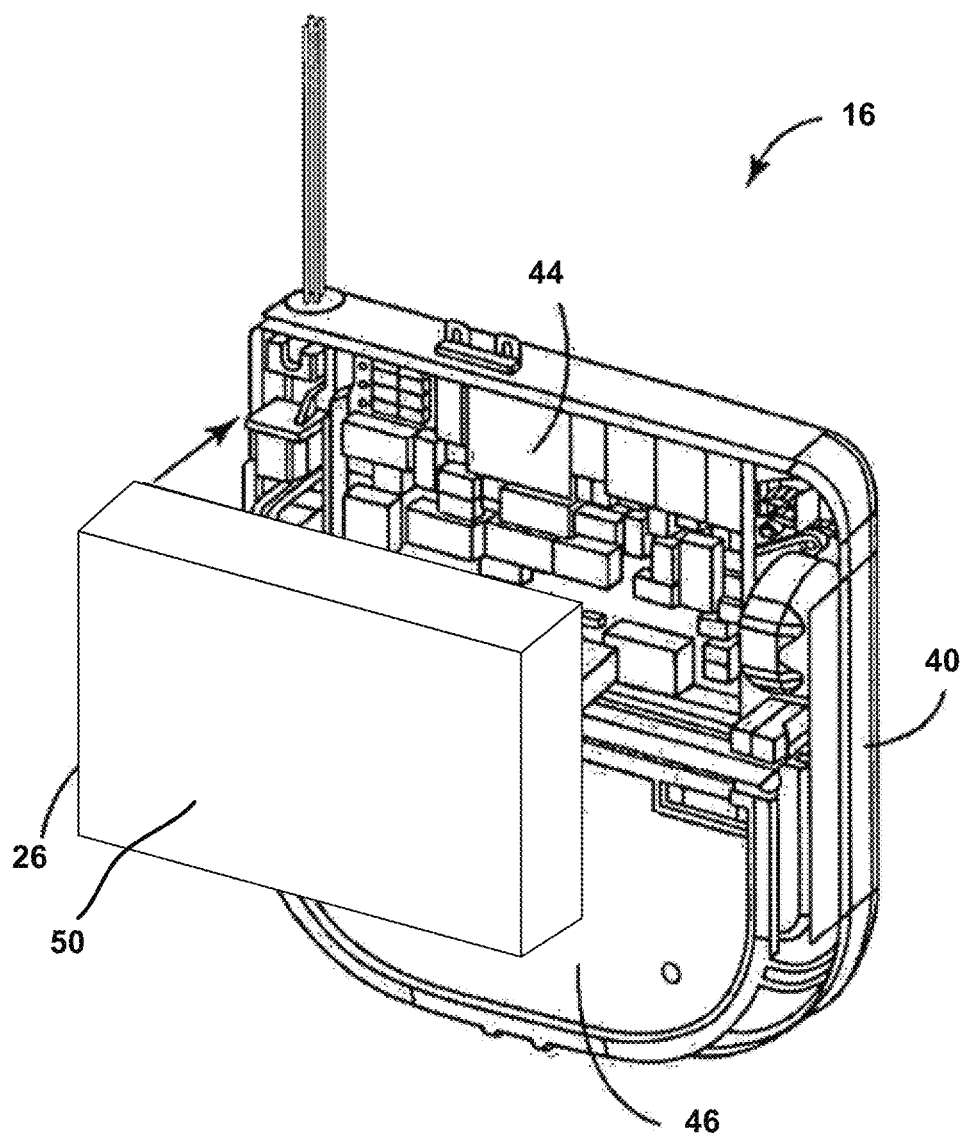
FIG. 2 is a conceptual diagram illustrating a partial exploded view of the IMD of FIG. 1.

FIG. 2 is a conceptual diagram of IMD 16 of FIG. 1 with connector block 42 not shown and a portion of outer housing 40 removed to illustrate some of the internal components within housing 40. IMD 10 includes outer housing 40, a control circuitry 44 (which may include processing circuitry), energy storage device assembly 26 (e.g., including an organic electrolyte battery) and capacitor(s) 46. Control circuitry 44 may be configured to control one or more sensing and/or therapy delivery processes from IMD 16 via leads 18, 20, and 22 (not shown in FIG. 2). Energy storage device assembly 26 includes foil pack 50 disposed around (e.g., forming a liquid and/or hermetic enclosure) one or more electrochemical cells that provide operational power to IMD 16. In the example IMD 16 of FIG. 2, energy storage device 26 charges capacitor(s) 46 and powers control circuitry 44.

During fabrication of energy storage device assembly 26, two laminated foil substrates may be positioned with the electrodes (anode and cathode) between the two foil substrates. The two laminated foil substrates may be heat sealed together (e.g., around the perimeter) to form foil pack 50 to enclose the electrodes within foil pack 50. An electrolyte may be introduced into the enclosure before the heat sealing or added after the heat sealing (e.g., via one or more fill ports in the foil package). As shown and described below, each electrode may include a conductive tab that extends from the current collectors of the electrode across the heat sealed boundary to outside the foil pack enclosure to allow for energy to be transferred out of the foil pack enclosure. In some examples, the conductive tab for one or more of the electrodes may be integrally formed with the current collector for the respective electrode, e.g., as part of the same conductive metal sheet.

Figure 3A:
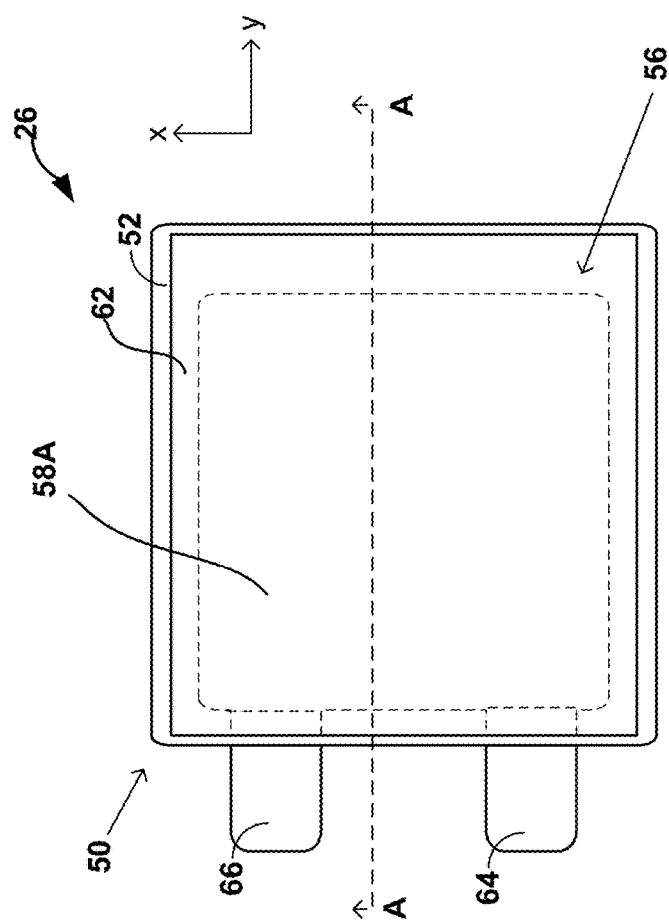
FIGS. 3A-3C are conceptual schematic diagrams illustrating an example energy assembly in accordance with examples of the disclosure.
Figure 3B:
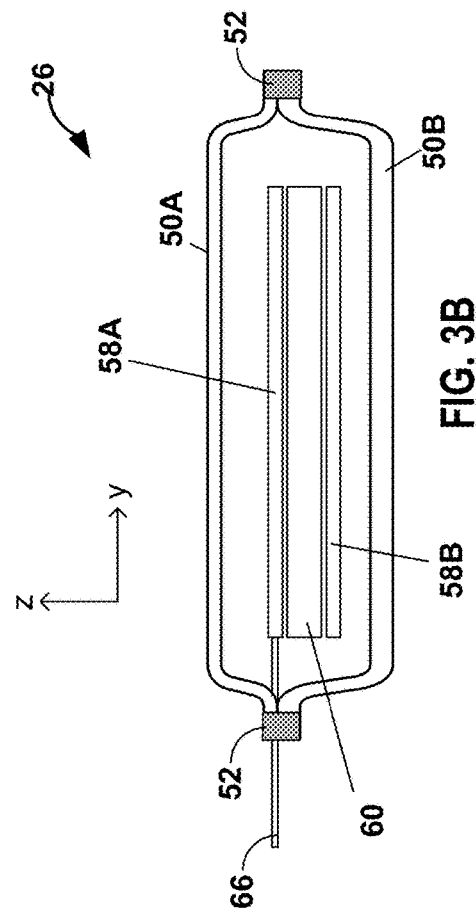

FIG. 3A is a conceptual schematic diagram illustrating an example energy storage device assembly 26 from a plan view in accordance with examples of the disclosure. FIG. 3B is a conceptual schematic diagram illustrating energy storage device assembly 26 along cross-section A-A shown in FIG. 3A.

As shown, assembly 26 includes foil pack 50 enclosing stack of electrodes 56 within enclosure 62 defined by foil pack 50. Foil pack 50 includes first foil substrate 50A and second foil substrate 50B heat sealed to each other around electrodes 56. Although not shown, first and second foil substrates 50A, 50B may have a laminate or multi-layer structure that allows for substrates 50A and 50B to be heat sealed to each other. For example, first foil substrate 50A and second foil substrate 50B may each include a metallic layer with a polymer layer on either side of the metallic layer. The metallic layer may be any suitable material such as aluminum or stainless steel, and may function as a barrier layer for foil pack 50. The polymer layer on the side of the metallic layer that bonds to the opposing substrate (the polymer layer that bonds with the opposing substrate) may be a polyolefin such as polyethylene (PE) although other polymer materials are contemplated. The polymer material may be melt-able/bondable via the application of heat (e.g., at a temperature above the melting point of the polymer) and/or electrically insulating. The polymer layer on the side of the metallic layer opposite the bonding interface may include stronger higher melting material such as a polyester (PET) although other polymer materials are contemplated. The polymer material may add strength to the foil pack 50 and/or may also be electrically insulating. The structure of first foil substrate 50A and second foil substrate 50B may allow for first foil substrate 50A and second foil substrate 50B to be bonded to each other via a heat-sealing process. The description for the metals, thicknesses, and polymer layers are exemplary, and other suitable examples are contemplated. The techniques described herein may apply regardless of the particle foil and lamination type selected.

Figure 3C:
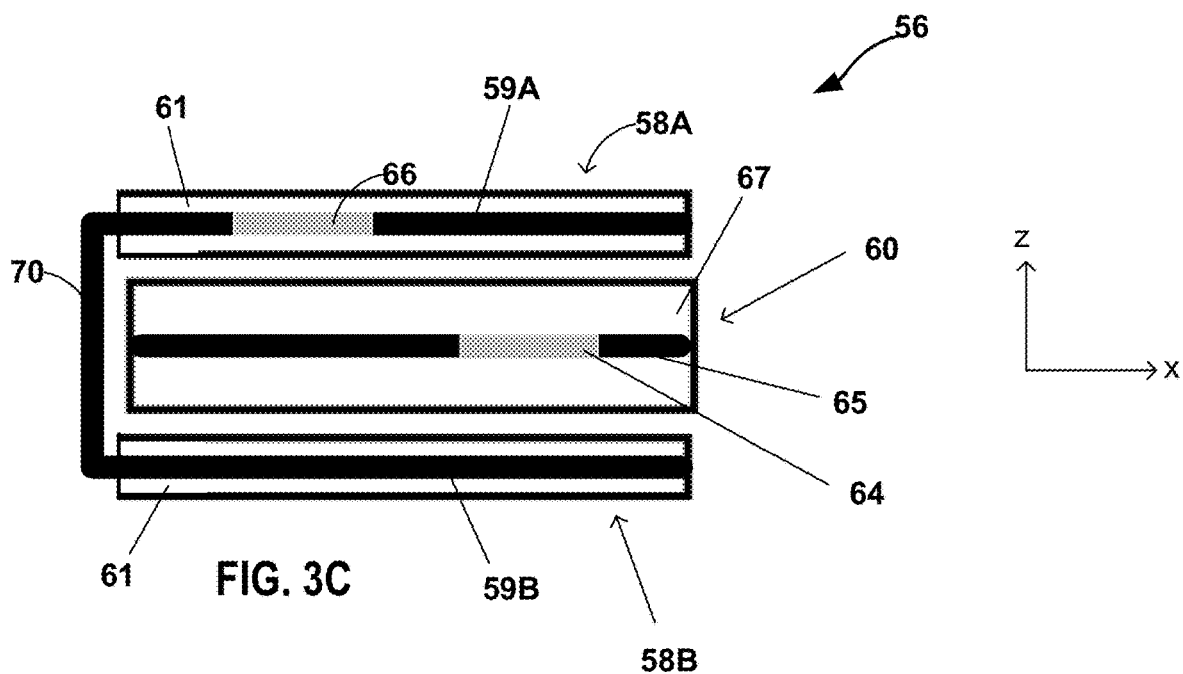

Although not individually labelled in FIG. 3A, stack of electrodes 56 within enclosure 26 includes an anode and a cathode. The anode may include first anode plate 60, and the cathode may include second cathode plate 58A and third cathode plate 58B within enclosure 62 of foil pack 50. As illustrated in FIG. 3C, anode plate 60 includes anode current collector 65 with anode active material 67 disposed on the top and bottom of collector 65. As illustrated in FIG. 3C, second cathode plate 58A includes cathode current collector 59A with cathode active material 61 disposed on the top and bottom of collector 59A, and third cathode plate 58B includes cathode current collector 59B with cathode active material 61 disposed on the top and bottom of collector 59B. As described further below, second cathode plate 58A and third cathode plate 58B may be connected by connector 70, e.g., with connector 70 and current collectors 59A, 59B being formed from the same sheet of material.

Example materials used to form the current collector 59A, 59B, and 65 may be any useful conductive material such as titanium, aluminum, nickel (e.g., for the anode current collector), copper and/or alloys thereof. In some examples, anode current collector 65 may be formed of titanium, nickel, copper, or alloys thereof (e.g., Ti alloy, Ni alloy, or copper alloy), and second and third current collectors 59A and 59B may be formed of titanium, aluminum, or alloys thereof. Other metal or suitable conductive materials are also contemplated. While first, second, and third current collector 65, 59A, 59B are shown with a rectangular shape, other shapes are contemplated. Each current collector of electrodes 56 may have the same or different shape as the other current collector plates.

As noted above, anode current collector 65 of anode plate 60 may include a surface coating of a first active material 67. Second current collectors 59A and third current collector plate 59B of second cathode plate 58A and third cathode plate 58B, respectively, may each include a surface coating of second active material 61. The first active material on anode current collector 65 may comprise the active material of the anode and may be referred to herein as the anode active material. The second active material 61 on second current collector 59A and third current collector 59B may comprise the active material of the cathode and may be referred to herein as the cathode active material. The active material may be on one or both major surface of the current collectors of electrodes 56. Example active materials for an anode may include lithium, graphite, lithium titanate and/or the like. Example active materials for a cathode may include silver vanadium oxide, CFx, MnO2, and mixtures of thereof. Example electrolyte that may be employed in the electrochemical cell may include organic electrolytes containing lithium hexafluoroarsenate salt. Other materials are contemplated.

Although not shown in FIGS. 3A and 3B, a separator may be positioned between one or more of the electrode plates, and an electrolyte such as a liquid electrolyte may be present within enclosure 62 defined by foil pack 50 such that the electrolyte surrounds electrodes 56 and the separator. An example electrolyte that may be employed in the electrochemical cell may include organic electrolytes containing lithium hexafluoroarsenate salt but other electrolyte materials are contemplated. Together, the electrolyte and electrodes 56 may form an electrochemical cell that provide operational power to IMD 16. In some examples, the electrochemical cell defined by electrodes 56, the separator, and the electrolyte in enclosure 62 may be a lithium ion cell.

First conductor tab 64 extends from current collector 65, and is electrically coupled to first anode plate 60. First conductor tab 64 defines an electrically conductive surface and may not be coated with the first active material 67 that coats first current collector 65. In some examples, first conductor tab 64 is integrally formed with first current collector 65 (e.g., with both conductor tab 64 and first current collector 65 being formed from the same metallic sheet). As shown in FIG. 3A, first conductor tab 64 extends out of enclosure 62 defined by foil pack 50 with heat seal 52 being formed around first conductor tab 64. This allows anode plate 60 to be electrically coupled to one or more components outside of foil pack 50, e.g., by electrically coupling first conductor tab 64 to the one or more components outside foil pack 50. Foil pack 50 is considered to partially enclose the anode in the example of FIGS. 3A and 3B since first conductive tab 64 extends across heat seal 52 with a portion outside of enclosure 26 and first anode plate 60 being within enclosure 26.

Second conductor tab 66 extends from second current collector 59A, and is electrically coupled to second cathode plate 58A. Second conductor tab 66 defines an electrically conductive surface and may not be coated with the second active material 61 that coats second current collector 59A. In some examples, second conductor tab 66 is integrally formed with second current conductor 59A (e.g., with both conductor tab 66 and second current collector 59A being formed from the same metallic sheet rather than being separate components welded or otherwise attached to each other). As shown in FIG. 3A, second conductor tab 66 extends out of enclosure 62 defined by foil pack 50 with heat seal 52 being formed around second conductor tab 66 (e.g., as illustrated partially in FIG. 3B). This allows second cathode plate 58A to be electrically coupled to one or more components outside of foil pack 50, e.g., by electrically coupling second conductor tab 66 to the one or more components outside foil pack 50. Foil pack 50 is considered to partially enclose the cathode in the example of FIGS. 3A and 3B since second conductive tab 66 extends across heat seal 52 with a portion outside of enclosure 26 and second cathode plate 58A being within enclosure 26.

Second cathode plate 58A is connected both electrically and physically to third cathode plate 58B by connector 70. Rather than having a separate conductive tab extending directly from third cathode plate 58B out of foil pack 50, third cathode plate 58B is electrically coupled to second conductive tab 66 by connector 70 and second cathode plate 58A. In this manner, only a single conductive tab may extend out of foil pack for the cathode even though there are multiple cathode plates 58A and 58B. As described below, in some examples, second current collector 59A, connector 70, and third current collector 59B may be integrally formed, e.g., from the same metallic sheet rather than being separate components welded or otherwise attached to each other.

First anode plate 60, second cathode plate 58A and third cathode plate 58B may have any suitable dimensions. In the examples of FIGS. 3A and 3B, first anode plate 60, second cathode plate 58A and third cathode plate 58B may have substantially the same surface area in the x-y plane, while first anode plate 60 may be thicker than second cathode plate 58A and third cathode plate 58B in the z-direction. As described above, the multiple cathode plate design may increase the power of battery 26, and may allow for less in-plane cathode expansion which may reduce the risk of stressing the polymer encasement seal of foil pack 50 and breaching the cell. In some examples, the thickness of second cathode plate 58A (the total thickness of active material 61 and current collector 58A) and/or third cathode plate 58B (the total thickness of active material 61 and current collector 58B) may be less than the thickness of first cathode plate 60 (the total thickness of active material 67 and current collector 65). In some examples, the combined thickness of second cathode plate 58A and third cathode plate 58B may be substantially the same as first anode plate 60, e.g., so that the overall volume of second cathode plate 58A and third cathode plate 58B is substantially the same as first anode plate 60.

In one example with a single cathode plate and a single anode plate, the total thickness of the cathode plate may be on the order of about 0.08 inches thick to about 0.16 inches thick, e.g., for a pacemaker battery. Other medium rate batteries may be thicker (e.g., about 0.32 inches total for the cathode plate). The overall cathode plate thickness may also expand in the thickness (z) direction and may also be a consideration for stressing the seal 62 of foil pack 50. In some examples, thicker cathode plates will expand more. For efficient packaging that includes margins for in-plane cathode expansion, individual cathode plate thickness (e.g., for cathode plate 58A or cathode plate 58B) may be below about 0.040 inches, e.g., about 0.020" thick. In the case of a cell that has an overall target of about 0.1 inches thick cathode total to provide energy to the device, the design may include four cathode plates that are about 0.025 inches thick. For thicker cells with thicker overall cathode, example may include more plates to reduce the individual plate thickness into a reasonable range.

FIG. 3C is a conceptual schematic diagram of electrodes 56 from a side view facing first conductive tab 64 and second conductive tab 66 with foil pack 50 not shown. As shown, second cathode plate 58A is folded over third cathode plate 58B about connector 70. In the folder configuration, the outer perimeters of second cathode plate 58A and third cathode plate 58B may be substantially aligned with each other. In other examples, the outer perimeters of second cathode plate 58A and third cathode plate 58B may be offset from one another in the folder configuration.

In the example of FIG. 3C, second cathode plate 58A and third cathode plate 58B are folded about connector 70 with first anode plate 60 being sandwiched between second cathode plate 58A and third cathode plate 58B. In such an example, connector 70 has a length that is greater than the thickness of first anode plate 60 to allow for such positioning. FIG. 10 is a conceptual schematic diagram illustrating another example in which second cathode plate 58A and third cathode plate 58B are folded over each other about connector 70 but first anode plate 60 is positioned adjacent to second cathode plate 58A and third cathode plate 58B but not between second cathode plate 58A and third cathode plate 58B.

Figure 4B:
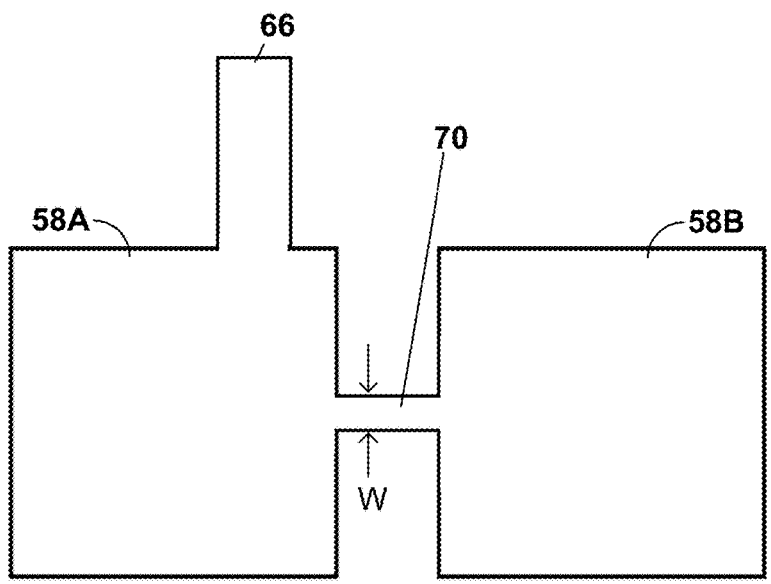
FIGS. 4A and 4B are conceptual schematic diagrams illustrating example electrodes in accordance with examples of the disclosure.
Figure 4A:
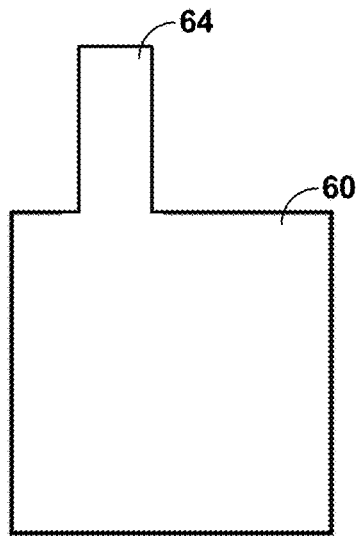

FIG. 4A is a conceptual schematic diagram of first anode plate 60 and first conductive tab 64 of energy storage device 26. As shown, first conductive tab 64 extends from first anode plate 60 so that first anode plate 60 is electrically and physically coupled to conductive tab 64. First current collector 65 and first conductive tab 64 may be integrally formed from the same metallic sheet by etching or otherwise selectively removing portions of the metallic sheet to provide the geometry shown in FIG. 4A.

FIG. 4B is a conceptual schematic diagram of second cathode plate 58A, third cathode plate 58B, connector 70, and second conductive tab 66 of energy storage assembly 26 shown in FIGS. 3A-3C. As described above, third cathode plate 58B may be electrically couple to second cathode plate 58A by way of connector 70 and, in turn, is also electrically coupled to conductive tab 66 by way of connector 70 and second cathode plate 58A. Unlike that shown in FIGS. 3A-3C, FIG. 4B shows second cathode plate 58A and third cathode plate 58B prior to being folded about connector 70. As described herein, current collector 59A of second cathode plate 58A, current collector 59B of third cathode plate 58B, connector 70, and second conductive tab 66 may be integrally formed with each other, e.g., from a single, substantially planar metallic sheet (or other sheet formed of suitable conductive material). In some examples, a single, substantially planar metallic sheet with a larger rectangular size may be selectively etched or otherwise have portions selectively removed to provide the geometry show in FIG. 4B.

Figure 13:
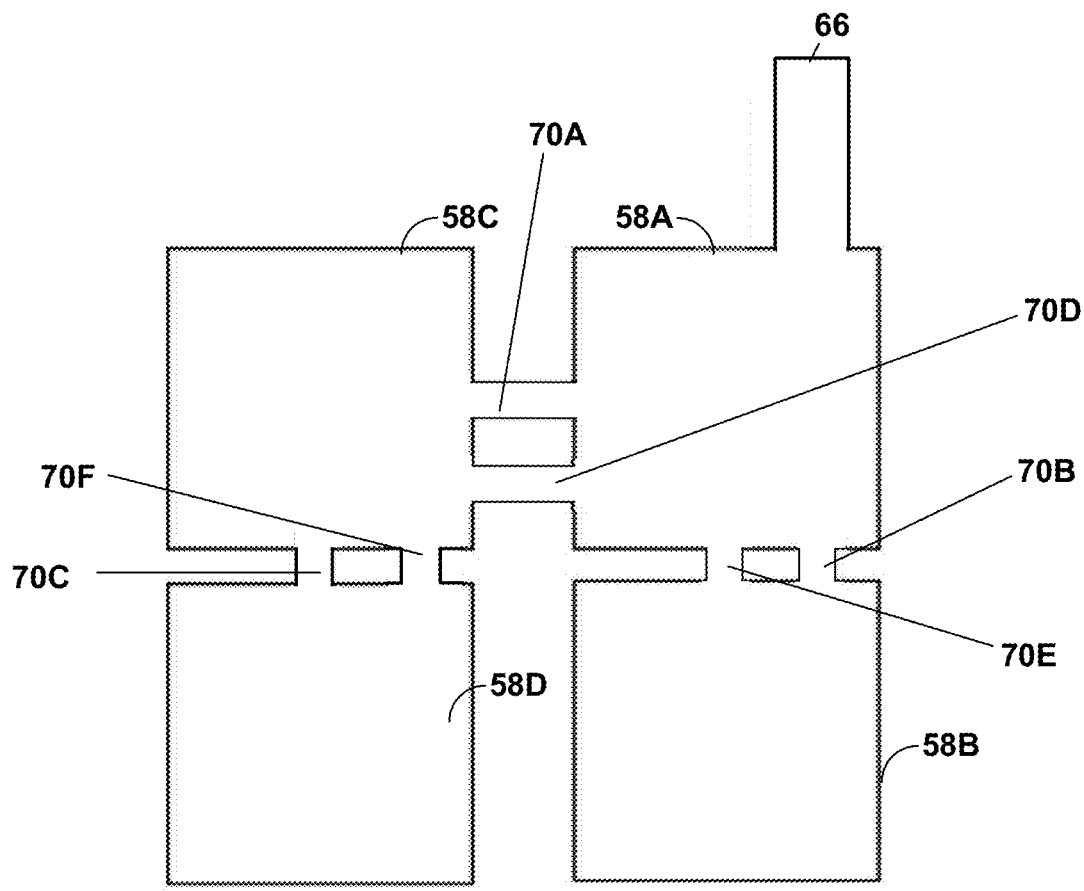

Connector 70 is located on a side of second cathode plate 58A adjacent to the side of second cathode plate with second conductive tab 66. Connector 70 does not span the entire width of second cathode plate 58A and third cathode plate 58B but instead has a smaller width, which may allow for easier folding of second cathode plate 58A over third cathode plate 58B. Connector 70 may be wide and/or thick enough to have mechanical integrity and be able to carry enough current. Both of these considerations depend on the material for the current collector and connector material (e.g., titanium, copper, aluminum, nickel, and alloys of the same). In some examples, connector 70 has a width, W, of about 0.05 inches to about 0.15 inches, which may be about 10 percent or less of the width of the adjacent current collectors of second cathode plate 58A and/or third cathode plate 58B. In some examples, only a single connector 70 connects second cathode plate 58A and third cathode plate 58B while in other examples more than one connector connects second cathode plate 58A and third cathode plate 58B, e.g., as shown in FIG. 13 with connectors 70A and 70D. The thickness of collector 70 may be about the same as the thickness of current collectors 58A and 58B. In some examples, the thickness in the z-direction of collector 70 may be about 0.0001 inches to about 0.005 inches, e.g., with the thickness of cathode plates 58A and 58B being about 0.02 inches to about 0.04 inches.

FIG. 5 is a conceptual schematic diagram showing another example configuration of second cathode plate 58A, third cathode plate 58B, connector 70, and second conductive tab 66. Unlike that shown in FIG. 4B, connector 70 is on the side of first cathode plate 58A opposite that of second tab 66.

In the example shown in FIG. 3C, second conductive tab 66 has a thickness in the z-direction that is substantially the same as that of the thickness of second current collector 59A. FIG. 6A is a conceptual schematic diagram showing another example in which the thickness T1 of second current collector 59A is greater than the thickness T2 of second conductive tab 66. The thinner profile of conductive tab 66 may correspond to the portion of conductive tab 66 over which heat seal 52 is formed over conductive tab 66, which may allow for a better seal around conductive tab 66. FIG. 6B is a conceptual diagram of conductive tab 66 along cross-section B-B of FIG. 6A. As shown, conductive tab 66 may have rounded edges and/or a non-rectangular cross-section (e.g., oval as compared to the rectangular cross-section show in FIG. 3C). The portion of tab 66 that gets sealed between the polymer of foil pack 50 may be easier to seal if tab 66 is thinner and/or has a more rounded cross section. First conductive tab 64 and anode current collector 60 may have a similar configuration to tab 66.

Tabs that are thinner than current collectors may provide one or more benefits. There may be different, sometimes competing, desirable properties acting on the collectors. Within the bulk of the cathode, for instance, it may be better to have a thicker current collector and/or cathode plate to handle the high pressures exerted on the part during fabrication (e.g., during a pressing operation). Conversely, it may be desirable for the portion that gets sealed between the polymer of the foil pack to be thinner so that it is easier to seal (in addition to a rounded cross-section).

FIG. 7A is a conceptual schematic diagram showing another example stack of electrodes 76 that may be employed in an energy storage device such as energy storage device 26 show in FIGS. 3A and 3B. The view of electrodes 76 is similar to that shown in FIG. 3C of electrodes 56 (the current collector and active materials for the respective plates are not shown in FIG. 7A) and aspects of electrodes 76 may be the same or substantially similar to that described for electrodes 56. However, unlike that of electrode stack 56, the cathode of electrodes 76 includes four cathode plates (second cathode plate 58A, third cathode plate 58B, fourth cathode plate 58C, and fifth cathode plate 58D) rather than two cathode plates. As shown in FIG. 7A, second cathode plate 58A, third cathode plate 58B, fourth cathode plate 58C, and fifth cathode plate 58D are folder over each other via connectors 70A, 70B, 70C, with first anode plate 60 of the anode being positioned between second cathode plate 58A and fourth cathode plate 58C. In other examples, first anode plate 60 may be between cathode plate 58A and cathode plate 58B, or between cathode plate 58C and cathode plate 58D. In some examples, changing from a two cathode plates design to a four cathode plate design (for the same plate area and battery capacity) may require that the higher plate count design have thinner cathode plates. Thinner cathode plates can be easier to manufacture, and less concerns about in-plane expansion (affects packaging efficiency and reliability).

FIG. 7B is a conceptual diagram showing the cathode without the respective current collector plates folded over each other. Like that described earlier, all or only some of the current collectors of cathode plates 58A-58D, connectors 70A-70C, and conductive tab 66 may be integrally formed, e.g., from the same metallic sheet prior to folding the sheet.

Figure 8:
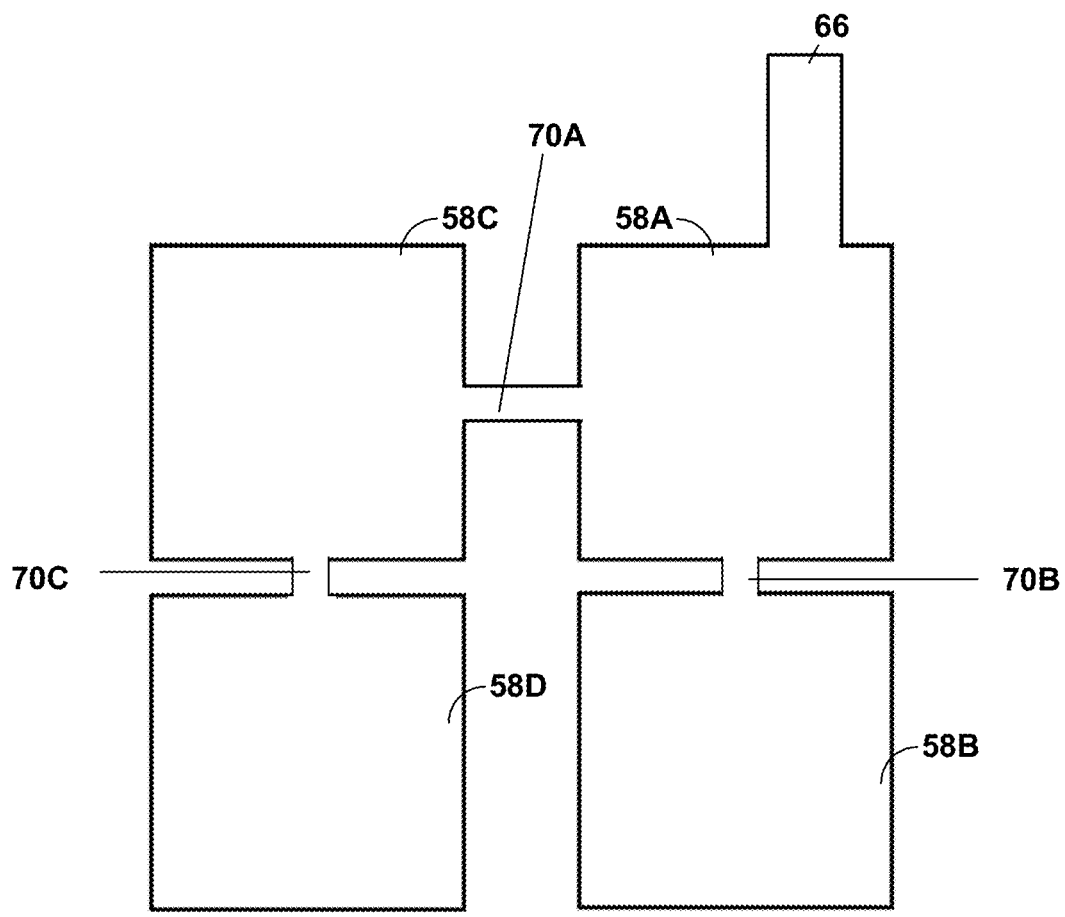
FIG. 8 is a conceptual schematic diagram illustrating another example electrode in accordance with examples of the disclosure.

FIG. 8 is a conceptual schematic diagram showing another example of the cathode for electrodes 76 of FIG. 7A but with connectors 70B and 70C being located on different sides of second cathode plate 58A and fourth cathode plate 58C, respectively, compared to that shown in FIG. 7B. The differences between cathode plate form in FIGS. 7B and 8 may come into play when considering handling a long unfolded part versus a "more square" unfolded part. Additionally, or alternatively, such differences may come in the die design for the cathode plate or in the sealing process. In some examples, the final design may be driven by the shape of the actual electrode plate. For example, in the case of an "inverted house" you may not want the tabs (70C and 70B from FIG. 8) to be at the "point" of the plate, and it may be more desirable to have them on the sides.

Figure 9:
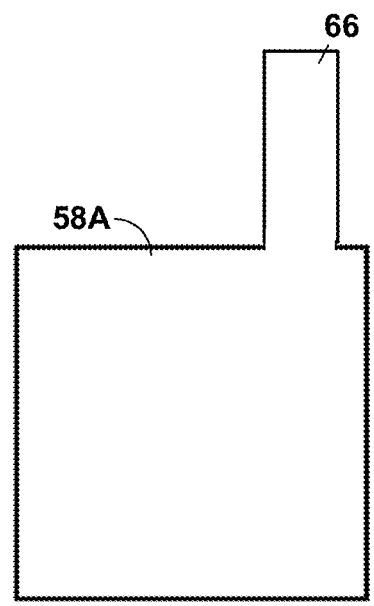
FIG. 9 is a conceptual schematic diagram illustrating another example electrode in accordance with examples of the disclosure.

FIG. 9 is a conceptual schematic diagram showing another example of the cathode for electrodes of energy storage device 26. Unlike that of the cathodes previously described the cathode in FIG. 9 includes only second cathode plate 58A with second conductive tab 66 extending therefrom. Second conductive tab 66 may be integrally formed with second cathode plate 58A and may be combined with an anode formed of a single anode plate and single conductive tab like first cathode plate 60 and first tab 64. In other examples, an electrode stack may be employed in which the cathode includes only a single plate and single conductive tab but with the anode including multiple plates and only single conductive tab, e.g., like that described for the example cathodes herein. However, in some examples, there may not be a benefit to having a design like FIGS. 7 and 8 but with multiple anodes folded upon themselves, e.g., as those anode surfaces would essentially not be accessible for discharge. That may not be the case for a design like that shown in FIG. 3, e.g., with two outer anode plates and a central cathode plate. The same considerations for in-plane cathode swelling may apply and thus the benefit for having thinner cathodes. As mentioned, one example may include a design with a single thick cathode with two (or more) opposing (e.g., directly opposing) anode plates.

FIGS. 11 and 12 are conceptual schematic diagrams showing other example cathodes that may be employed for energy storage device 26 with each example having second cathode plate 58A connected to third cathode plate 58B by connector 70, and second conductive tab 66 extending from second cathode plate 58A. When incorporated into an energy storage device like device 26, second cathode plate 58A may be folder over third cathode plate 58B by connector 70. The location of connector 70 is a difference between the example of FIG. 11 and FIG. 12.

FIG. 10 is a conceptual schematic diagram showing the example cathode of FIG. 11 as part of an electrode stack 86. Unlike that of electrodes 56 in FIG. 3C, first anode plate 60 is located adjacent to second cathode plate 58A and third cathode plate 58B but without first anode plate 60 being between second cathode plate 58A and third cathode plate 58B. Thus, length of connector 70 may be less than other examples in which first anode plate 60 is between two of the cathode plates. In some examples, for such a design, by not bending the cathode across the anode plate, there may not be a chance of there being stress from the cathode tab on the adjacent separator layers. The bend of cathode connector across the anode plate may be less risky than a bend of an anode connector across the cathode plate because the cathode swells and can increase the stress during discharge. Accommodation (additional insulation or space) may need to be factored in when an anode connector is bent across the cathode.

FIG. 13 is a conceptual schematic diagram showing the example cathode design that is an alternative to the example cathode design shown in FIG. 8. As shown, each cathode plate 58A-58D is connected by more than one connector 70A-70F, e.g., with two connectors 70A-70F connecting each cathode plate 58A-58D. Such a design may allow for less resistance to current being conducted between the plates and/or a more rigid design that allows for easier bending since the plates are anchored at two points rather than one. In some examples, as long as the cross-sectional area is reduced for each connector, it can have the same bending stiffness as a single connector. It may also have the benefit of equaling out the current distribution throughout the plate. One of the primary benefits of having two or more connectors between cathode plates is that there is less of a chance that a cathode plate can rotate out of position if there are multiple connectors, especially if those connectors are at the opposite ends of the plate.

Figure 14:
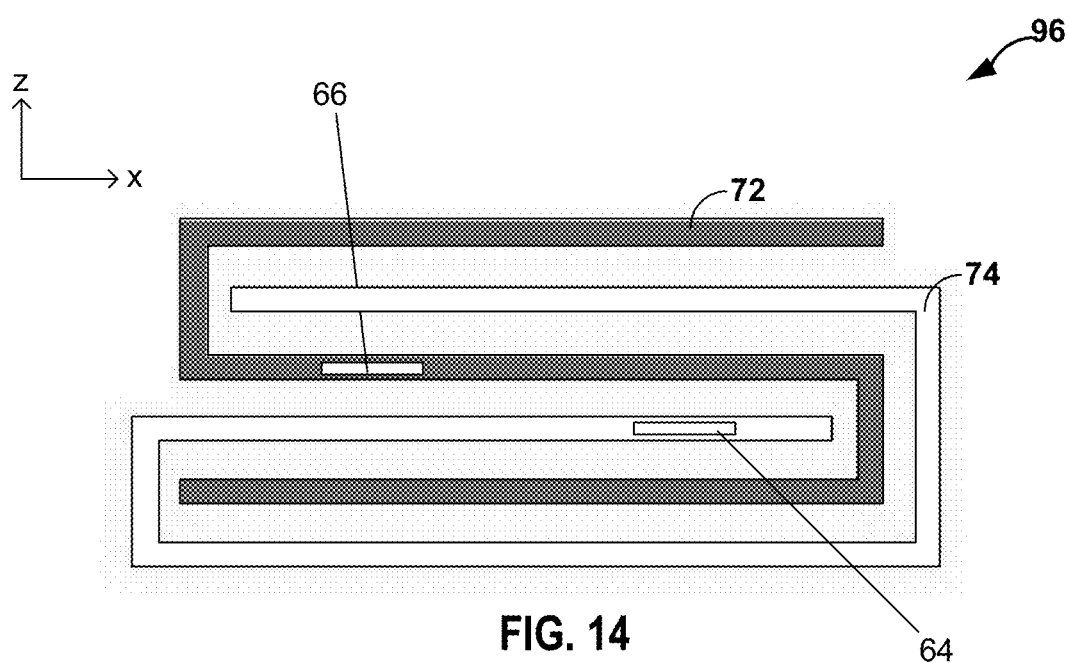

FIG. 14 is a conceptual diagram illustrating another example stack of electrodes 96 that may be employed in an energy storage device such as device 26. Electrodes 96 include cathode 72 and anode 74. The view shown in FIG. 14 is a side view similar to that shown in FIG. 3C for electrodes 56. Unlike that of electrodes 56, in the example of FIG. 14, both cathode 72 and anode 74 have a folded plate design rather than only the cathode as in the example of FIG. 3C. In the example of FIG. 14, the vertical portions of cathode 72 and anode 74 may correspond to connector such as connector 70 and the horizontal portions may correspond to electrode plates like first anode plate 60 and second cathode plate 58A. In the example of FIG. 14, a portion of cathode 72 is positioned between respective plates of anode 74 and a portion of anode 74 is positioned between respective plates of cathode 72. In some examples, the increased complexity of the design of FIG. 14 may allow for an increase the face-to-face area between anode and cathode plates and, thus, the power of the cell.

Figure 15:
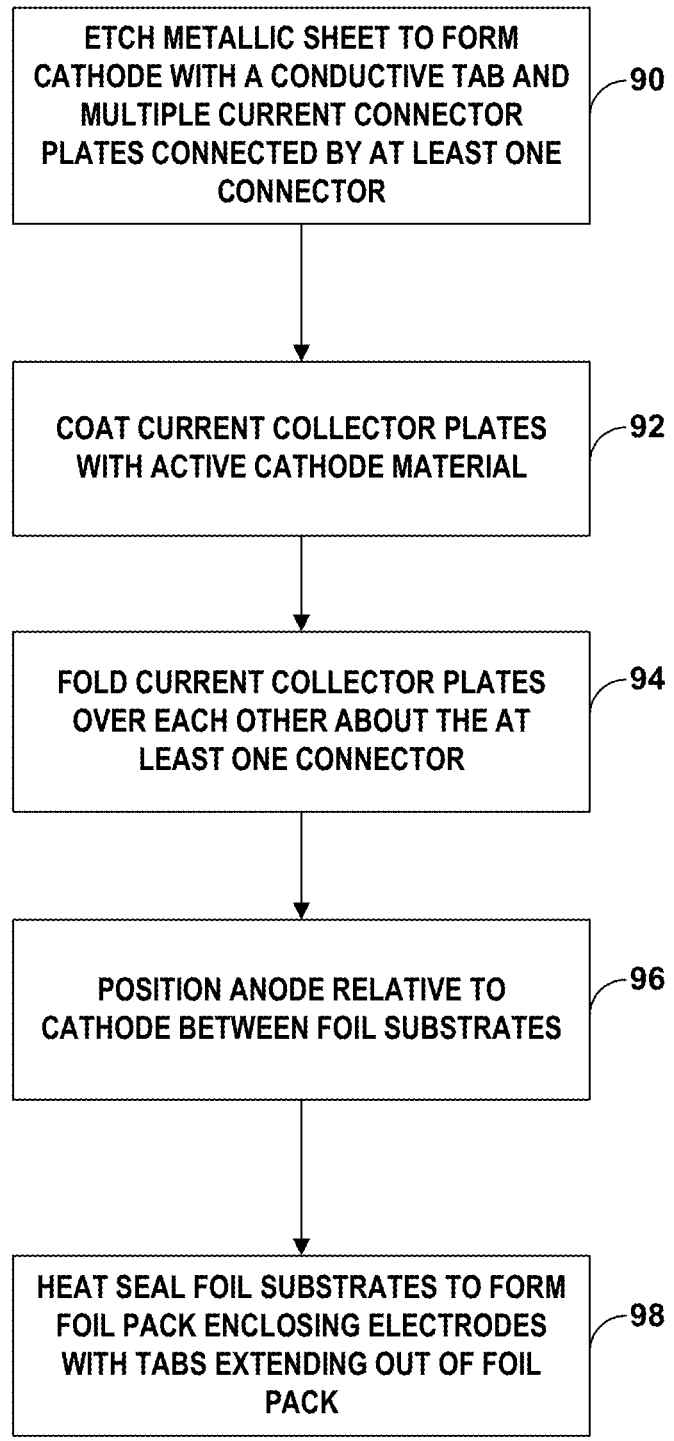
FIG. 15 is a flow diagram illustrating an example technique in accordance with examples of the disclosure.

FIG. 15 is a flow diagram illustrating an example technique for forming an example energy storage device assembly in accordance with some examples of the disclosure. For ease of description, the technique of FIG. 15 is described with regard to assembly 26 of FIGS. 3A and 3B. However, such an example may be used to form any suitable energy storage device assembly in accordance with the other examples described herein.

As shown in FIG. 15, a substantially planar metallic sheet formed of a suitable material for a cathode current collector may be etched to selectively remove portions of the sheet to form a conductive member with second conductive tab 66, second current collector 59A, third current collector 59B, and connector 70 as shown in FIG. 4B (90). Suitable etching processes may include chemical etching. The etching solution may be selected by the composition of the current collectors, e.g., with titanium being removed with a mixture of HF and $HNO_3$. In other examples, the portions of the metallic sheet may be selectively removed by a process other than etching, such as, die cutting or stamping. In some examples, the cathode and anode may be formed with non-perforated sheets (which still could be etched) but lend themselves more to stamping. The cathode could be a.

Following the etching process, second current collector 59A and third current collector 59B may be coated with a cathode active material 61 using any suitable technique (92). Example techniques may include pressed power, paste, or slurry deposition, for example. Example active cathode materials 61 include those described above. In other examples, the portions of the metallic sheet corresponding second cathode plate 58A and third cathode plate 58B may be coated prior to step 90 in FIG. 15. Connectors 70 and/or tabs 66 may be left uncoated in some examples. In a pressed powder or paste process, the connectors 70 and tabs 66 may be left bare. A slurry coating process may include covering the connectors 70 and tabs 66, and the active material may or may not be subsequently ablated from the tabs 66 and/or connectors 70. However, for applications that involve slurry coating (like lithium ion), the tabs may be wider or possibly the full length of the edge. Also, the cathode and/or anode plates created by a slurry coating process may be thinner (e.g., about 0.005 inch thick electrodes with 10 to 20 micron current collector foils). In some examples, it may be possible to make pressed powder secondary (rechargeable) batteries using the designs describes herein. In another examples, a pre-pressed sheet of cathode active material may be employed (without collector) that is then subsequently pressed onto a current collector.

Once coated with an active cathode material, second cathode plate 58A and third cathode plate 58 may be folded over each other about connector 70 (94). This may be accomplished by automated (e.g., by robotics) or manual manipulation of second cathode plate 58A and third cathode plate 58B. Once folded, first anode plate 60 may be positioned between second cathode plate 58A and third cathode plate 58B (96). In other examples, second cathode plate 58A and third cathode plate 58B may be folded around first anode plate 60 in a single step rather than two steps.

Electrodes 56 may then be positioned between first foil substrate 50A and second foil substrate 50B. Heat seal 52 may then be formed between first foil substrate 50A and second foil substrate 50B to partially enclose electrodes 56 in enclosure 62 with conductive tabs 64 and 66 extending across heat seal 52 out of enclosure 62 (98). In some examples, first foil substrate 50A and second foil substrate 50B may be already partially heat sealed, e.g., on three sides, to form a pocket into which electrodes 56 are positioned and then another heat sealing process is performed to seal the final side with tabs 64, 66 extending therethrough.

Any suitable heat-sealing process may be used to form first heat seal 52. For example, first foil substrate 50A and second foil substrate 50B may be sealed by either a single sided heat source on one side of the seal or an opposed heat source on both sides of the seal. In the case of substrates having the example multi-layer structure described above, heat conducts through the PET and Al layers to reach the PE layer. The opposing PE layers melt together. Opposed heating may be preferable for sealing around tabs 64 and 66.

Although not shown in FIG. 15, an electrolyte may be provided within enclosure 62, e.g., by using a fill port in foil pack 50 after heat seal 52 is formed or introducing the electrolyte prior to or during the sealing process. Once assembly 26 is formed, tabs 64, 66 may be electrically coupled to one or more electrical components of IMD 16 so that operational energy generated by electrodes 56 and the electrolyte may be transmitted outside foil pack 50 via tabs 64, 66.

Various examples have been described in this disclosure. These and other examples are within the scope of the following clauses and claims.

Clause 1. An assembly comprising: a first electrode comprising a first conductive tab, a first current collector, and a first active material on the first current collector; a second electrode comprising a second conductive tab, a second current collector, a third current collector, a second active material on the second current collector and the third current collector, and at least one connector connecting the second current collector to the third current collect, wherein the second current collector and the third current collector are folded over each other about the at least one connector, wherein the second conductive tab is coupled to the second current collector, and wherein the third current collector is electrically coupled to second conductive tab via the at least one connector and the second current collector; and a foil package being sealed over the first conductive tab and the second conductive tab to partially enclose the first electrode and second electrode.

Clause 2. The assembly of clause 1, wherein the second current collector and the third current collector are folded over the first current collector such that the first current collector is positioned between the second current collector and the third current collector.

Clause 3. The assembly of any one of clauses 1 or 2, wherein the first current collector is positioned adjacent to the second current collector and the third current collector but not between the second current collector and the third current collector.

Clause 4. The assembly of any one of clauses 1-3, wherein a thickness of the second conductive tab is reduced where the foil package is sealed over the second conductive tab compared to the thickness of the tab directly adjacent to the second current collector within the enclosure of the foil pack.

Clause 5. The assembly of any one of clauses 1-4, wherein the second conductive tab is integrally formed with the second current collector.

Clause 6. The assembly of any one of clauses 1-5, wherein the second conductive tab is integrally formed with the second current collector, the at least one connector, and the third current collector.

Clause 7. The assembly of any one of clauses 1-6, wherein the at least one connector comprises at least one first connector, wherein the first electrode further comprises a fourth current collector connected to the first current collector by at least one second connector, wherein the first current collector and the fourth current collector are folded over each other about the at least one second connector, wherein the fourth current collector is electrically coupled to first conductive tab via the at least one second connector and the first current collector.

Clause 8. The assembly of clause 7, wherein the at least one of the first current collector or the fourth current collector is positioned between the second current collector and the third current collector.

Clause 9. The assembly of any one of clauses 1-8, wherein the at least one connector comprises more than one connector connecting the second current collector to the third current collector.

Clause 10. The assembly of any one of clauses 1-9, wherein a width of the at least one connector is less than a width of the second current collector and a width of the third current collector.

Clause 11. The assembly of any one of clauses 1-10, wherein the at least one connector comprises at least one first connector, wherein the second electrode further comprising a fourth current collector and a fifth current collector, wherein the fourth current collector is connected to the second current collector and folded over the second current collector by at least one second connector, wherein the fifth current collector is connected to the third current collector and folded over the third current collector by at least one third connector, and wherein the fourth current collector and the fifth current collector are electrically coupled to the second conductive tab.

Clause 12. The assembly of any one of clauses 1-11, wherein the first electrode comprises an anode and the second electrode comprises a cathode.

Clause 13. The assembly of any one of clauses 1-12, wherein a thickness of the first current collector combined with the first active material is greater than a thickness of the second current collector combined with the second active material and a thickness of the third current collector combined with the second active material.

Clause 14. The assembly of any one of clauses 1-13, wherein the second conductive tab has a rounded cross-section where the foil package is sealed over the second conductive tab.

Clause 15. A method comprising: positioning a first electrode relative to a second electrode, wherein the first electrode comprises a first conductive tab, a first current collector, and a first active material on the first current collector, and wherein the second electrode comprises a second conductive tab, a second current collector, a third current collector, a second active material on the second current collector and the third current collector, and at least one connector connecting the second current collector to the third current collect, wherein the second current collector and the third current collector are folded over each other about the at least one connector, wherein the second conductive tab is coupled to the second current collector, and wherein the third current collector is electrically coupled to second conductive tab via the at least one connector and the second current collector; and heat sealing a foil package over the first conductive tab and the second conductive tab to partially enclose the first electrode and second electrode.

Clause 16. The method of clause 15, wherein forming the assembly comprises: folding the second current collector over the third current collector by the at least one connector; and subsequently heat sealing at least a portion of the foil pack to form the heat seal over the first conductive tab and the second conductive tab.

Clause 17. The method of any one of clauses 15 or 16, wherein the second current collector and the third current collector are folded over the first current collector such that the first current collector is positioned between the second current collector and the third current collector.

Clause 18. The method of any one of clauses 15-17, wherein positioning the first electrode relative to the second electrode comprises positioning the first current collector adjacent to the second current collector and the third current collector but not between the second current collector and the third current collector.

Clause 19. The method of any one of clauses 15-18, wherein a thickness of the second conductive tab is reduced where the foil package is sealed over the second conductive tab compared to the thickness of the tab directly adjacent to the second current collector within the enclosure of the foil pack.

Clause 20. The method of any one of clauses 15-19, wherein the second conductive tab is integrally formed with the second current collector.

Clause 21. The method of any one of clauses 15-20, wherein the second conductive tab is integrally formed with the second current collector, the at least one connector, and the third current collector.

Clause 22. The method of any one of clauses 15-21, wherein the at least one connector comprises at least one first connector, wherein the first electrode further comprises a fourth current collector connected to the first current collector by at least one second connector, wherein the first current collector and the fourth current collector are folded over each other about the at least one second connector, wherein the fourth current collector is electrically coupled to first conductive tab via the at least one second connector and the first current collector.

Clause 23. The method of clause 22, wherein the at least one of the first current collector or the fourth current collector is positioned between the second current collector and the third current collector.

Clause 24. The method of any one of clauses 15-23, wherein the at least one connector comprises more than one connector connecting the second current collector to the third current collect.

Clause 25. The method of any one of clauses 15-24, wherein a width of the at least one connector is less than a width of the second current collector and a width of the third current collector.

Clause 26. The method of any one of clauses 15-25, the at least one connector comprises at least one first connector, wherein the second electrode further comprising a fourth current collector and a fifth current collector, wherein the fourth current collector is connected to the second current collector and folded over the second current collector by at least one second connector, wherein the fifth current collector is connected to the third current connector and folded over the third current collector by at least one third connector, and wherein the fourth current collector and the fifth current collector are electrically coupled to the second conductive tab.

Clause 27. The method of any one of clauses 15-26, wherein the first electrode comprises an anode and the second electrode comprises a cathode.

Clause 28. The method of any one of clauses 15-27, wherein a thickness of the first current collector combined with the first active material is greater than a thickness of the second current collector combined with the second active material and a thickness of the third current collector combined with the second active material.

Clause 29. The method of any one of clauses 15-28, wherein the second conductive tab has a rounded cross-section where the foil package is sealed over the second conductive.

Clause 30. A medical device including the battery assembly of any one of clauses 1-14, the battery assembly configured to provide operational power to the medical device.

Clause 31. The medical device of clause 30, wherein the medical device comprises an implantable medical device configured to deliver electrical stimulation to a patient and/or sense electrical signals of the patient using the operational power from the battery assembly.

The invention claimed is:

1. An assembly comprising:
a first electrode comprising a first conductive tab, a first current collector, and a first active material on the first current collector;
a second electrode comprising a second conductive tab, a second current collector, a third current collector, a second active material on the second current collector and the third current collector, and at least one connector connecting the second current collector to the third current collect,
wherein the second current collector and the third current collector are folded over each other about the at least one connector,
wherein the second conductive tab is coupled to the second current collector, and
wherein the third current collector is electrically coupled to second conductive tab via the at least one connector and the second current collector; and
a foil package being sealed over the first conductive tab and the second conductive tab to partially enclose the first electrode and second electrode,
wherein the second current collector has a first major surface and a second major surface generally opposing the first major surface, wherein the second current collector defines a first thickness from the first major surface and the second major surface,
wherein the third current collector has a third major surface and a fourth major surface generally opposing the third major surface, wherein the third current collector defines a second thickness from the third major surface and the fourth major surface,
wherein the at least one connector extends between a first side of the second current collector and a second side of the third current collector, wherein the first side of the second current collector defines a first width extending in a direction substantially orthogonal to the first thickness of the second current collector, wherein the second side of the third current collector defines a second width extending in a direction substantially orthogonal to the second thickness of the third current collector,
wherein the at least one connector defines a third width adjacent to first side extending in the direction substantially orthogonal to the first thickness of the second current collector, wherein the at least one connector defines a fourth width adjacent to second side extending in the direction substantially orthogonal to the second thickness of the third current collector,
wherein the third width of the at least one connector is less than the first width of the first side such that the at least one connector does not span the entire first width of the first side of the second current collector, and wherein the fourth width of the at least one connector is less than the second width of the second side such that the at least one connector does not span the entire second width of the second side of the third current collector.

2. The assembly of claim 1, wherein the second current collector and the third current collector are folded over the first current collector such that the first current collector is positioned between the first major surface of the second current collector and the third major surface of the third current collector and such that an outer perimeter of the first current collector is substantially aligned with an outer perimeter of the first major surface of the second current collector and with an outer perimeter of the third major surface of the third current collector.

3. The assembly of claim 1, wherein the first current collector is positioned adjacent to the second current collector and the third current collector but not between the first major surface of the second current collector and the third major surface of the third current collector.

4. The assembly of claim 1, wherein the second conductive tab has a thickness extending in a direction substantially parallel with the first thickness of the second current collector, wherein the thickness of the second conductive tab is reduced where the foil package is sealed over the second conductive tab compared to the thickness of the second conductive tab directly adjacent to the second current collector within the enclosure of the foil pack.

5. The assembly of claim 1, wherein the second conductive tab is integrally formed with the second current collector.

6. The assembly of claim 1, wherein the second conductive tab is integrally formed with the second current collector, the at least one connector, and the third current collector.

7. The assembly of claim 1, wherein the at least one connector comprises at least one first connector, wherein the second current collector and the third current collector are folded over each other about the at least one first connector in a first direction, wherein the first electrode further comprises a fourth current collector connected to the first current collector by at least one second connector, wherein the first current collector and the fourth current collector are folded over each other about the at least one second connector in a second direction different than the first direction, wherein the fourth current collector is electrically coupled to first conductive tab via the at least one second connector and the first current collector.

8. The assembly of claim 7, wherein the at least one of the first current collector or the fourth current collector is positioned between the first major surface of the second current collector and the third major surface of the third current collector.

9. The assembly of claim 1, wherein the at least one connector comprises more than one connector connecting the second current collector to the third current collector.

10. The assembly of claim 1, wherein the at least one connector comprises at least one first connector,
wherein the second electrode further comprising a fourth current collector and a fifth current collector, wherein the fourth current collector is connected to the second current collector and folded over the second current collector by at least one second connector,
wherein the fifth current collector is connected to the third current collector and folded over the third current collector by at least one third connector, and
wherein the fourth current collector and the fifth current collector are electrically coupled to the second conductive tab.

11. The assembly of claim 1, wherein the first electrode comprises an anode and the second electrode comprises a cathode.

12. The assembly of claim 1, wherein a thickness of the first current collector combined with the first active material is greater than the first thickness of the second current collector combined with the second active material and the second thickness of the third current collector combined with the second active material.

13. The assembly of claim 1, wherein the second conductive tab has a rounded cross-section where a heat seal of the foil package extends around the second conductive tab.

14. A method comprising:
positioning a first electrode relative to a second electrode, wherein the first electrode comprises a first conductive tab, a first current collector, and a first active material on the first current collector, and wherein the second electrode comprises a second conductive tab, a second current collector, a third current collector, a second active material on the second current collector and the third current collector, and at least one connector connecting the second current collector to the third current collect,
wherein the second current collector and the third current collector are folded over each other about the at least one connector,
wherein the second conductive tab is coupled to the second current collector, and
wherein the third current collector is electrically coupled to second conductive tab via the at least one connector and the second current collector; and
heat sealing a foil package over the first conductive tab and the second conductive tab to partially enclose the first electrode and second electrode,
wherein the second current collector has a first major surface and a second major surface generally opposing the first major surface, wherein the second current collector defines a first thickness from the first major surface and the second major surface,
wherein the third current collector has a third major surface and a fourth major surface generally opposing the third major surface, wherein the third current defines a second thickness from the third major surface and the fourth major surface,
wherein the at least one connector extends between a first side of the second current collector and a second side of the third current collector, wherein the first side of the second current collector defines a first width extending in a direction substantially orthogonal to the first thickness of the second current collector, wherein the second side of the third current collector defines a second width extending in a direction substantially orthogonal to the second thickness of the third current collector,
wherein the at least one connector defines a third width adjacent to first side extending in the direction substantially orthogonal to the first thickness of the second current collector, wherein the at least one connector defines a fourth width adjacent to second side extending in the direction substantially orthogonal to the second thickness of the third current collector,
and
wherein the third width of the at least one connector is less than the first width of the first side such that the at least one connector does not span the entire first width of the first side of the second current collector, and wherein the fourth width of the at least one connector is less than the second width of the second side such that the at least one connector does not span the entire second width of the second side of the third current collector.

15. The assembly of claim 1, wherein the at least one connector comprises at least one first connector, wherein the second electrode further comprises a fourth current collector, wherein the fourth current collector is connected to the second current collector and folded over the second current collector by at least one second connector, wherein the fourth current collector is electrically coupled to the second conductive tab,
wherein the second current collector is positioned between the third current collector and the fourth current collector.

16. The assembly of claim 1, wherein the at least one connector comprises at least one first connector, wherein the second electrode further comprises a fourth current collector, wherein the fourth current collector is connected to the second current collector and folded over the second current collector by at least one second connector, wherein the fourth current collector is electrically coupled to the second conductive tab,
wherein the second current collector and the third current collector are folded over each other about the at least one first connector in a first direction, and
wherein the fourth current collector and the second current collector are folded over each other about the at least one second connector in a second direction different than the first direction.

17. The assembly of claim 16, wherein the second direction is opposite the first direction and runs substantially parallel to the first direction.

18. The assembly of claim 16, wherein the second direction is perpendicular the first direction.

19. The assembly of claim 1, wherein the at least one connector comprises only a single connector extending between the second current collector and the third current collector.

20. The assembly of claim 1, wherein the second conductive tab is the only portion of the second electrode extending outside of a seal of the foil package.

21. The assembly of claim 1, wherein the third width is substantially the same at the fourth width.

* * * * *